United States Patent
Gao et al.

(10) Patent No.: US 11,193,883 B2
(45) Date of Patent: Dec. 7, 2021

(54) KITS FOR DETECTING CONTENT OF FLUORIDE IONS IN MICROSAMPLES

(71) Applicant: Harbin Medical University, Heilongjiang (CN)

(72) Inventors: Yanhui Gao, Heilongjiang (CN); Simeng Huo, Heilongjiang (CN); Wei Wang, Heilongjiang (CN); Yanmei Yang, Heilongjiang (CN); Dianjun Sun, Heilongjiang (CN); Yumei Fan, Heilongjiang (CN); Huazhu Yan, Heilongjiang (CN); Qun Lou, Heilongjiang (CN); Limei Wang, Heilongjiang (CN); Ning Guo, Heilongjiang (CN)

(73) Assignee: Harbin Medical University, Harbin (CN)

( * ) Notice: Subject to any disclaimer, the term of this patent is extended or adjusted under 35 U.S.C. 154(b) by 298 days.

(21) Appl. No.: 16/449,346

(22) Filed: Jun. 22, 2019

(65) Prior Publication Data
US 2020/0080933 A1 Mar. 12, 2020

(30) Foreign Application Priority Data

Sep. 6, 2018 (CN) .......................... 201811038788.X

(51) Int. Cl.
| | | |
|---|---|---|
| *G01N 21/31* | (2006.01) | |
| *B01L 3/00* | (2006.01) | |
| *G01N 1/38* | (2006.01) | |
| *G01N 21/75* | (2006.01) | |
| *G01N 33/18* | (2006.01) | |
| *G01N 21/78* | (2006.01) | |

(52) U.S. Cl.
CPC ............ *G01N 21/31* (2013.01); *B01L 3/5085* (2013.01); *G01N 1/38* (2013.01); *G01N 21/75* (2013.01); *G01N 33/18* (2013.01); *B01L 2300/0893* (2013.01); *G01N 21/78* (2013.01)

(58) Field of Classification Search
CPC .......... G01N 21/31; G01N 1/38; G01N 21/75; G01N 33/18; G01N 21/78; G01N 31/22; B01L 3/5085; B01L 2300/0893
See application file for complete search history.

(56) References Cited

U.S. PATENT DOCUMENTS

2008/0248593 A1 10/2008 Ezan et al.

FOREIGN PATENT DOCUMENTS

| CN | 101806744 A | 8/2010 |
| CN | 104677899 A | 6/2015 |
| KR | 20090067862 A | * 6/2009 |

OTHER PUBLICATIONS

Brunzie, Gerald F., and Ronald T. Pflaum, "The direct spectrophotometric determination of fluoride ion", 1962, Proceedings of the Iowa Academy of Science. vol. 69. No. 1. (Year: 1962).*
Hashitani et al., "Direct determination of fluoride in water by use of acetylacetone as a demasking agent", 1979, Bunseki Kagaku, 28, 11, 680-685. (Year: 1979).*
Translation of KR20090067862A, Choo, Yoon Hyun et al., Jun. 25, 2009 (Year: 2009).*
Translation of CN101806744A, Hong, Ling-Cheng, Aug. 18, 2010 (Year: 2010).*
Translation of CN104677899A, Lin, Dong-Yue et al., Jun. 3, 2015 (Year: 2015).*

* cited by examiner

*Primary Examiner* — Samuel P Siefke
*Assistant Examiner* — Henry H Nguyen

(57) ABSTRACT

Disclosed is a kit for detecting content of fluoride ions in a microsample, including: at least one 96-well plate, reagent A, reagent B, reagent C, reagent D, reagent E and a fluoride standard solution having a concentration of 2.5 mg/L. The kit can be used to effectively overcome the uncertainties in the existing methods for detecting fluoride ions, and also involves rapid and convenient operation. Moreover, this method involves simple and rapid operation, the use of a small amount of a sample and simultaneous detection of multiple samples. This kit provides a more standardized detection to lower the human error, thereby allowing for a more reliable result and for a suitable application in the on-site detection of content of fluoride ions in various environments such as in water quality engineering or in the laboratory.

4 Claims, No Drawings

KITS FOR DETECTING CONTENT OF FLUORIDE IONS IN MICROSAMPLES

CROSS REFERENCE TO RELATED APPLICATIONS

This application claims the benefit of priority from Chinese Patent Application No. 201811038788.X, filed on Sep. 6, 2018. The content of the aforementioned application, including any intervening amendments thereto, is incorporated herein with reference in its entirety.

TECHNICAL FIELD

The application relates to chemical detection, and particularly to a kit for detecting content of fluoride ions in a microsample, and more particularly to a kit for detecting fluoride ions within a certain concentration range in water or a liquid microsample which is colorless and transparent after pretreatment.

BACKGROUND

For the detection of content of fluoride ions in water, the National Standard discloses several methods, including spectrophotometry, ion selective electrode method, ion chromatography and visual colorimetry with zirconium alizarinsulfonate.

Regarding the spectrophotometry, an alizarin complexone and a lanthanum nitrate are introduced to react with the fluoride to form a blue complex, of which the color intensity is linearly correlated with the content of fluoride ions in a certain range. This method is performed by a spectrophotometer. The defects of this method include large single sample amount, requirement of manual operation and strict control of pH during the preparation of the detecting liquid.

In the ion selective electrode method, the lanthanum fluoride monocrystal shows selectivity to fluoride ions, resulting in a potential difference between different concentrations of fluorine solutions on both sides of the lanthanum fluoride film. This potential difference is generally called a film potential, which is related to the ion activity of the fluoride solution. The fluorine electrode and the saturated calomel electrode constitute a pair of galvanic batteries, and the concentration of fluoride ions in the water sample can be directly determined according to the linear relationship between the potential and the negative logarithm of the ion activity. This method requires a fluoride ion selective electrode, a saturated calomel electrode, a precision pH-meter and an electromagnetic stirrer. However, this method involves disadvantages of large single sample amount, complicated and time-consuming detection process and susceptibility to ions and temperature.

As for the ion chromatography, the target anion in the water sample is eluted into the ion exchange system with a system of carbonate and bicarbonate. Since various anions have their respective retention times in the analytical column, the target anion can be separated and determined. The separated anions are converted into carbonic acid with high electrical conductivity after passing through cation exchange column or a suppressor system, such that various anions in the water sample can be simultaneously analyzed. The conductivity of individual anion components is measured by a conductivity detector, where the relative retention time and the peak height or area are respectively used for qualification and quantification. An ion chromatograph instrument is necessary for this method. However, this method still has some defects such as high requirement for the instrument, complicated operation and requirement of manual operation.

With respect to the visual colorimetry with zirconium alizarinsulfonate, sodium alizarine sulfonate reacts with a zirconium salt under an acidic condition to form a red complex, while in the presence of fluoride ions, a colorless zirconium fluoride is formed to discolor the solution, which can be quantified by visual colorimetry. However, this method prefers relatively pure water, which is not suitable for practical application.

However, there are still various uncertainties in the implementation of such methods. For example, during the operation, there may be difference in reagents of different batches; and the manual operation may result in some interference in the preparation of a detecting liquid, the adjustment of pH of a buffer solution and the plotting of a standard curve. Therefore, a certain difference may exist in the results obtained by different laboratories and even in the results obtained by different people in the same laboratory. Given the above, there is an urgent need to overcome the above defects.

SUMMARY

An object of the application is to provide a set of a kit for detecting content of fluoride ions in a microsample to overcome the uncertainties in the prior art, standardizing and unifying the detection to make the results more reliable.

The application provides a kit for detecting content of fluoride ions in a microsample, comprising: at least one 96-well plate, reagent A, reagent B, reagent C, reagent D, reagent E and a fluoride standard solution having a concentration of 2.5 mg/L;

wherein the reagent A is an analytical acetone; the reagent B is an analytical acetylacetone; the reagent C is a solution having a pH of 5.0 and containing 0.05 mol/L of alizarin complexone; the reagent D is a solution having a pH of 4.1 and containing sodium acetate; and the reagent E is a solution having a pH of 4.1 and containing 0.05 mol/L of lanthanum nitrate.

In an embodiment, the reagent C is prepared by a method, comprising the following steps:

adding 1.927 g of the alizarin complexone to a 100 mL beaker; adding 5 mL of deionized water by a micropipette; then dropwise adding 5-15 mL of 1 mol/L sodium hydroxide solution to dissolve the alizarin complexone; after the alizarin complexone is dissolved, adding 0.625 g of sodium acetate to produce a mixture, and adjusting the mixture to pH 5.0 with 1 mol/L hydrochloric acid solution followed by dilution to 100 mL with deionized water to produce the reagent C containing 0.05 mol/L of the alizarin complexone.

In an embodiment, the reagent D is prepared by a method, comprising the following steps:

dissolving 3.5 g of sodium acetate in 80 mL of deionized water; adding 7.5 mL of glacial acetic acid followed by dilution to 100 mL with deionized water to produce a mixture; then adjusting the mixture to pH 4.1 with an acetic acid or sodium hydroxide solution using a pH meter to produce the reagent D.

In an embodiment, the reagent E is prepared by a method, comprising the following steps:

weighing 2.215 g of solid lanthanum nitrate; dropwise adding 3-8 mL of a hydrochloric acid solution to dissolve the solid lanthanum nitrate to produce a mixture; and adjusting the mixture to pH 4.1 with 1 mol/L sodium acetate followed by dilution to 100 mL with deionized water to produce the reagent E containing 0.05 mol/L of the lanthanum nitrate.

The application further provides a method of detecting content of fluoride ions using the kit of the invention, comprising:

(1) mixing 7 parts by volume of the reagent A, 2 parts by volume of the reagent B, 2 parts by volume of the reagent C and 2 parts by volume of the reagent D uniformly followed by mixing 2 parts by volume of the reagent E to produce a detecting liquid for use;

(2) selecting 8 wells in the 96-well plate as main wells and denoting the main wells as wells A, B, C, D, E, F, G and H, respectively; and adding different amounts of the fluoride standard solution to the main wells followed by dilution to 100 μL with deionized water; wherein concentrations of the fluoride ions in the main wells are 0 mg/L in well A, 0.039 mg/L in well B, 0.078 mg/L in well C, 0.156 mg/L in well D, 0.313 mg/L in well E, 0.625 mg/L in well F, 1.25 mg/L in well G and 2.5 mg/L in well H, respectively; wherein this process specifically comprises the steps of: adding 200 μL of the 2.5 mg/L fluoride standard solution to the well H and adding 100 μL of deionized water to each of the rest main wells; transferring 100 μL of the 2.5 mg/L fluoride standard solution in the well H to the well G followed by mixing to produce a mixture G; accurately transferring 100 μL of the mixture G to the well F followed by mixing to produce a mixture F; treating the rest main wells sequentially in the same manner; and discarding 100 μL of the mixture B instead of transferring it to the well A; and selecting some of the rest wells of the 96-well plate as secondary wells followed by addition of 100 μL of a sample to respective wells; and (3) adding 150 μL of the detecting liquid prepared in step (1) to respective main wells and secondary wells for complete reaction; after 5 min, transferring the 96-well plate to a microplate reader and measuring the absorbance at 650 nm within 20 min; plotting a standard curve according to the absorbance and the fluoride ion concentrations in respective main wells to calculate concentrations of fluoride ions in the samples in respective secondary wells.

Compared to the prior art, the application has the following beneficial effects.

1. The invention develops a detection method using a novel kit to avoid deviations caused by human factors during the preparation of the detecting liquid and the buffer solution, enabling a more standardized, unified and reliable detection.

2. The conventional methods for detecting content of fluoride ions in water generally involve the use of a large amount of the sample (generally greater than 10 mL for a single sample) and the reagent (generally greater than 10 mL for a single sample). Moreover, these methods cannot enable simultaneous detection of multiple samples and require a long time for detection (generally more than 5 min for a single sample). Therefore, these methods fail to enable the miniaturization and kitization of the accurate, rapid, small-sample and high-throughput detection. However, the miniaturization and kitization of the method for detecting content of fluoride ions in water are achieved herein by selecting an appropriate instrument, wavelength, concentration of the fluoride standard solution, concentration and formulation of the detecting liquid, protective agent and buffer solution.

DETAILED DESCRIPTION OF EMBODIMENTS

The application will be further described below with reference to the embodiments, and the advantages and features of the application will become more apparent. However, these embodiments are merely illustrative of the invention and are not intended to limit the invention. It should be understood that any modifications and replacements made by those skilled in the art without departing from the spirit and scope of the invention should still fall within the scope of the invention.

Example 1 Preparation of a Kit

The kit included a 96-well plate, reagent A, reagent B, reagent C, reagent D, reagent E and a fluoride standard solution having a concentration of 2.5 mg/L, where the reagent A was an analytical acetone and the reagent B was an analytical acetylacetone.

The reagent C was prepared as follows. 1.927 g of alizarin complexone was weighed in a 100 mL beaker, added with 5 mL of deionized water by a micropipette, and then dropwise added with 5-15 mL of 1 mol/L sodium hydroxide solution to dissolve the alizarin complexone. After the alizarin complexone was dissolved, 0.625 g of sodium acetate was added to produce a mixture. The mixture was adjusted to pH 5.0 with 1 mol/L hydrochloric acid and diluted to 100 mL with deionized water to produce the reagent C containing 0.05 mol/L of the alizarin complexone.

The reagent D was prepared as follows. 3.5 g of sodium acetate was dissolved in 80 mL of deionized water, added with 7.5 mL of glacial acetic acid, diluted to 100 mL with deionized water and adjusted to pH 4.1 with an acetic acid solution or a sodium hydroxide solution using a pH meter to produce the reagent D.

The reagent E was prepared as follows. 2.215 g of solid lanthanum nitrate was weighed, dropwise added with 3-8 mL of a hydrochloric acid solution, adjusted to pH 4.1 with a sodium acetate solution (1 mol/L) and diluted to 100 mL with deionized water to produce the reagent E containing 0.05 mol/L of the lanthanum nitrate.

Example 2

A fluoride standard solution having a concentration of 0.5 mg/L was used herein as sample 1 and the kit prepared in Example 1 was employed to detect the content of fluoride ions in sample 1, where 8 main wells were selected for the plotting of a standard curve and 20 secondary wells were selected for the detection of sample 1.

(1) Preparation of a Detecting Liquid 2,100 μL of the reagent A, 600 μL of the reagent B, 600 μL of the reagent C and 600 μL of the reagent D were mixed uniformly, added with 600 μL of the reagent E and mixed uniformly to produce the detecting liquid for use.

(2) Loading 8 wells in a 96-well microplate were selected as main wells, where the last well, i.e., the well H, was added with 200 μL of the 2.5 mg/L fluoride standard solution and the wells A-G were respectively added with 100 μL of deionized water. Then 100 μL of the fluoride standard solution in the well H was accurately transferred to the well G by a micropipette and mixed to produce a mixture and 100 μL of the mixture G was accurately transferred by a micropipette to the well F and mixed to produce a mixture F. The rest main wells were sequentially treated in the same manner, until 100 μL of the mixture B was discarded instead of transferring it to the well A. Thus, the liquid in each main well was 100 μL, and fluoride ion concentrations in the wells A-H were 0 mg/L, 0.039 mg/L, 0.078 mg/L, 0.156 mg/L, 0.313 mg/L, 0.625 mg/L, 1.25 mg/L and 2.5 mg/L, respectively.

20 wells among the rest wells in the 96-well microplate were selected as secondary wells and respectively added with 100 µL of the sample 1 (a fluoride standard solution having a known concentration of 0.5 mg/L).

(3) Detection of Content of Fluoride Ions

150 µL of the detecting liquid prepared in (2) was separately added to all of the 28 wells for reaction. After 5 min, the 96-well microplate was transferred to a microplate reader, and the absorbance was measured at 650 nm within 20 min. The results were shown in Table 1.

TABLE 1

Absorbance of the sample 1 at 650 nm

| ID | Column 1 (main wells) | Column 2 (secondary wells) | Column 3 (secondary wells) | Column 4 (secondary wells) |
|---|---|---|---|---|
| A | 0.092 | 0.141 | 0.142 | 0.141 |
| B | 0.096 | 0.142 | 0.142 | 0.143 |
| C | 0.099 | 0.142 | 0.141 | 0.142 |
| D | 0.107 | 0.142 | 0.142 | 0.141 |
| E | 0.121 | 0.141 | 0.141 | |
| F | 0.152 | 0.142 | 0.141 | |
| G | 0.212 | 0.143 | 0.142 | |
| H | 0.338 | 0.141 | 0.143 | |

A standard curve was plotted based on the fluoride contents in the wells A-H in the column 1 (respectively 0 mg/L, 0.039 mg/L, 0.078 mg/L, 0.156 mg/L, 0.313 mg/L, 0.625 mg/L, 1.250 mg/L and 2.500 mg/L) and the corresponding absorbance, where the regression equation was $y=0.0982x-0.0008$ with a regression coefficient $R^2$ of 0.9998.

The fluoride contents in the 20 secondary wells were calculated according to the above equation and shown in Table 2.

TABLE 2

Fluoride contents (mg/L) of the sample 1

| ID | Column 1 (main wells) | Column 2 (secondary wells) | Column 3 (secondary wells) | Column 4 (secondary wells) |
|---|---|---|---|---|
| A | 0 | 0.500 | 0.510 | 0.500 |
| B | 0.039 | 0.510 | 0.510 | 0.520 |
| C | 0.078 | 0.510 | 0.500 | 0.510 |
| D | 0.156 | 0.510 | 0.510 | 0.500 |
| E | 0.313 | 0.500 | 0.500 | |
| F | 0.625 | 0.510 | 0.500 | |
| G | 1.250 | 0.520 | 0.510 | |
| H | 2.500 | 0.500 | 0.520 | |

According to the above results, the average fluoride content of the sample 1 was calculated as 0.508 mg/L with standard deviation of 0.007 mg/L and variation coefficient of 1.38%.

Example 3

A fluoride standard solution having a concentration of 1.0 mg/L was used herein as sample 2 and the kit prepared in Example 1 was employed to detect the content of fluoride ions in sample 2, where 8 main wells were selected for the plotting of a standard curve and 20 secondary wells were selected for the detection of sample 2.

(1) Preparation of a Detecting Liquid 2,100 µL of the reagent A, 600 µL of the reagent B, 600 µL of the reagent C and 600 µL of the reagent D were mixed uniformly, added with 600 µL of the reagent E and mixed uniformly to produce the detecting liquid for use.

(2) Loading 8 wells in a 96-well microplate were selected as main wells, where the last main well, i.e., the well H, was added with 200 µL of the 2.5 mg/L fluoride standard solution and the wells A-G were respectively added with 100 µL of deionized water. Then 100 µL of the fluoride standard solution in the well H was accurately transferred to the well G by a micropipette and mixed to produce a mixture G, and 100 µL of the mixture G was accurately transferred by a micropipette to the well F and mixed to produce a mixture F. The rest main wells were sequentially treated in the same manner, until 100 µL of the mixture B was discarded instead of transferring it to the well A. Thus, the liquid in each main well was 100 µL, and fluoride ion concentrations in the wells A-H were 0 mg/L, 0.039 mg/L, 0.078 mg/L, 0.156 mg/L, 0.313 mg/L, 0.625 mg/L, 1.25 mg/L and 2.5 mg/L, respectively.

20 wells among the rest wells in the 96-well microplate were selected as secondary wells and respectively added with 100 µL of the sample 2 (a fluoride standard solution having a known concentration of 1.0 mg/L).

(3) Detection of Content of Fluoride Ions

150 µL of the detecting liquid prepared in (2) was separately added to all of the 28 wells for reaction. After 5 min, the 96-well microplate was transferred to a microplate reader, and the absorbance was measured at 650 nm within 20 min. The results were shown in Table 3.

TABLE 3

Absorbance of the sample 2 at 650 nm

| ID | Column 1 (main wells) | Column 2 (secondary wells) | Column 3 (secondary wells) | Column 4 (secondary wells) |
|---|---|---|---|---|
| A | 0.086 | 0.180 | 0.179 | 0.180 |
| B | 0.089 | 0.180 | 0.180 | 0.179 |
| C | 0.093 | 0.179 | 0.181 | 0.179 |
| D | 0.102 | 0.180 | 0.180 | 0.180 |
| E | 0.114 | 0.181 | 0.180 | |
| F | 0.143 | 0.180 | 0.180 | |
| G | 0.205 | 0.181 | 0.180 | |
| H | 0.321 | 0.181 | 0.181 | |

A standard curve was plotted based on the fluoride contents in the wells A-H in the column 1 (respectively 0 mg/L, 0.039 mg/L, 0.078 mg/L, 0.156 mg/L, 0.313 mg/L, 0.625 mg/L, 1.250 mg/L and 2.500 mg/L) and the corresponding absorbance, where the regression equation was $y=0.0938x-0.0009$ with a regression coefficient $R^2$ of 0.9997.

The fluoride contents in the 20 secondary wells were calculated according to the above equation and shown in Table 4.

TABLE 4

Fluoride contents of the sample 2 (mg/L)

| ID | Column 1 (main wells) | Column 2 (secondary wells) | Column 3 (secondary wells) | Column 4 (secondary wells) |
|---|---|---|---|---|
| A | 0.000 | 1.000 | 0.990 | 1.000 |
| B | 0.039 | 1.000 | 1.000 | 0.990 |
| C | 0.078 | 0.990 | 1.010 | 0.990 |
| D | 0.156 | 1.000 | 1.000 | 1.000 |
| E | 0.313 | 1.010 | 1.000 | |

TABLE 4-continued

Fluoride contents of the sample 2 (mg/L)

| ID | Column 1 (main wells) | Column 2 (secondary wells) | Column 3 (secondary wells) | Column 4 (secondary wells) |
|---|---|---|---|---|
| F | 0.625 | 1.000 | 1.000 | |
| G | 1.250 | 1.010 | 1.000 | |
| H | 2.500 | 1.010 | 1.010 | |

According to the above results, the average fluoride content of the sample 2 was calculated as 1.001 mg/L with standard deviation of 0.007 mg/L and variation coefficient of 0.669%.

Example 4

A fluoride standard solution having a concentration of 1.5 mg/L was used herein as sample 3 and the kit prepared in Example 1 was employed to detect the content of fluoride ions in sample 3, where 8 main wells were selected for the plotting of a standard curve and 20 secondary wells were selected for the detection of sample 3.

(1) Preparation of a Detecting Liquid 2,100 μL of the reagent A, 600 μL of the reagent B, 600 μL of the reagent C and 600 μL of the reagent D were mixed uniformly, added with 600 μL of the reagent E and mixed uniformly to produce the detecting liquid for use.

(2) Loading 8 wells in a 96-well microplate were selected as main wells, where the last well, i.e., the well H, was added with 200 μL of the 2.5 mg/L fluoride standard solution and the wells A-G were respectively added with 100 μL of deionized water. Then 100 μL of the fluoride standard solution in the well H was accurately transferred to the well G by a micropipette and mixed to produce a mixture and 100 μL of the mixture G was accurately transferred by a micropipette to the well F and mixed to produce a mixture F. The rest main wells were sequentially treated in the same manner, until 100 μL of the mixture B was discarded instead of transferring it to the well A. Thus, the liquid in each main well was 100 μL, and fluoride ion concentrations in the wells A-H were 0 mg/L, 0.039 mg/L, 0.078 mg/L, 0.156 mg/L, 0.313 mg/L, 0.625 mg/L, 1.25 mg/L and 2.5 mg/L, respectively.

20 wells among the rest wells in the 96-well microplate were selected as secondary wells and respectively added with 100 μL of the sample 3 (a fluoride standard solution having a known concentration of 1.5 mg/L).

(3) Detection of Content of Fluoride Ions

150 μL of the detecting liquid prepared in step (2) was separately added to all of the 28 wells for reaction. After 5 min, the 96-well microplate was transferred to a microplate reader, and the absorbance was measured at 650 nm within 20 min. The results were shown in Table 5.

TABLE 5

Absorbance of the sample 3 at 650 nm

| ID | Column 1 (main wells) | Column 2 (secondary wells) | Column 3 (secondary wells) | Column 4 (secondary wells) |
|---|---|---|---|---|
| A | 0.092 | 0.239 | 0.240 | 0.237 |
| B | 0.096 | 0.240 | 0.239 | 0.239 |
| C | 0.099 | 0.239 | 0.237 | 0.239 |
| D | 0.107 | 0.239 | 0.238 | 0.238 |
| E | 0.121 | 0.240 | 0.239 | |
| F | 0.152 | 0.238 | 0.240 | |
| G | 0.212 | 0.239 | 0.237 | |
| H | 0.338 | 0.241 | 0.239 | |

A standard curve was plotted based on the fluoride contents in the wells A-H in the column 1 (respectively 0 mg/L, 0.039 mg/L, 0.078 mg/L, 0.156 mg/L, 0.313 mg/L, 0.625 mg/L, 1.250 mg/L and 2.500 mg/L) and the corresponding absorbance, where the regression equation was $y=0.0982x-0.0008$ with a regression coefficient $R^2$ of 0.9998.

The fluoride contents in the 20 secondary wells were calculated according to the above equation and shown in Table 6.

TABLE 6

Fluoride contents (mg/L) of the sample 3

| ID | Column 1 (main wells) | Column 2 (secondary wells) | Column 3 (secondary wells) | Column 4 (secondary wells) |
|---|---|---|---|---|
| A | 0.000 | 1.500 | 1.510 | 1.480 |
| B | 0.039 | 1.510 | 1.500 | 1.500 |
| C | 0.078 | 1.500 | 1.480 | 1.500 |
| D | 0.156 | 1.500 | 1.489 | 1.489 |
| E | 0.313 | 1.510 | 1.500 | |
| F | 0.625 | 1.489 | 1.510 | |
| G | 1.250 | 1.500 | 1.480 | |
| H | 2.500 | 1.520 | 1.500 | |

According to the above results, the average fluoride content of the sample 2 was calculated as 1.498 mg/L with standard deviation of 0.011 mg/L and variation coefficient of 0.717%.

Example 5

A fluoride standard solution having a concentration of 2.0 mg/L was used herein as sample 4 and the kit prepared in Example 1 was employed to detect the content of fluoride ions in sample 4, where 8 main wells were selected for the plotting of a standard curve and 20 secondary wells were selected for the detection of sample 4.

(1) Preparation of a Detecting Liquid 2,100 μL of the reagent A, 600 μL of the reagent B, 600 μL of the reagent C and 600 μL of the reagent D were mixed uniformly, added with 600 μL of the reagent E and mixed uniformly to produce the detecting liquid for use.

(2) Loading 8 wells in a 96-well microplate were selected as main wells, where the last well, i.e., the well H, was added with 200 μL of the 2.5 mg/L fluoride standard solution and the wells A-G were respectively added with 100 μL of deionized water. Then 100 μL of the fluoride standard solution in the well H was accurately transferred to the well G by a micropipette and mixed to produce a mixture and 100 μL of the mixture G was accurately transferred by a micropipette to the well F and mixed to produce a mixture F. The rest main wells were sequentially treated in the same manner, until 100 μL of the mixture B was discarded instead of transferring it to the well A. Thus, the liquid in each main well was 100 μL, and fluoride ion concentrations in the wells A-H were 0 mg/L, 0.039 mg/L, 0.078 mg/L, 0.156 mg/L, 0.313 mg/L, 0.625 mg/L, 1.25 mg/L and 2.5 mg/L, respectively.

20 wells among the rest wells in the 96-well microplate were selected as secondary wells and respectively added with 100 μL of the sample 4 (a fluoride standard solution having a known concentration of 2.0 mg/L).

(3) Detection of Content of Fluoride Ions

150 μL of the detecting liquid four prepared in step (2) was separately added to all of the 28 wells for reaction. After 5 min, the 96-well microplate was transferred to a microplate reader, and the absorbance was measured at 650 nm within 20 min. The results were shown in Table 7.

TABLE 7

Absorbance of the sample 4 at 650 nm

| ID | Column 1 (main wells) | Column 2 (secondary wells) | Column 3 (secondary wells) | Column 4 (secondary wells) |
| --- | --- | --- | --- | --- |
| A | 0.090 | 0.282 | 0.282 | 0.283 |
| B | 0.094 | 0.281 | 0.283 | 0.282 |
| C | 0.097 | 0.281 | 0.282 | 0.281 |
| D | 0.104 | 0.282 | 0.281 | 0.280 |
| E | 0.119 | 0.283 | 0.280 | |
| F | 0.150 | 0.282 | 0.282 | |
| G | 0.210 | 0.280 | 0.282 | |
| H | 0.331 | 0.280 | 0.283 | |

A standard curve was plotted based on the fluoride contents in the wells A-H in the column 1 (respectively 0 mg/L, 0.039 mg/L, 0.078 mg/L, 0.156 mg/L, 0.313 mg/L, 0.625 mg/L, 1.250 mg/L and 2.500 mg/L) and the corresponding absorbance, where the regression equation was $y=0.0965x-0.0005$ with a regression coefficient $R^2$ of 1.

The fluoride contents in the 20 secondary wells were calculated according to the above equation and shown in Table 8.

TABLE 8

Fluoride contents of the sample 4 (mg/L)

| ID | Column 1 (main wells) | Column 2 (secondary wells) | Column 3 (secondary wells) | Column 4 (secondary wells) |
| --- | --- | --- | --- | --- |
| A | 0.000 | 2.000 | 2.000 | 2.010 |
| B | 0.039 | 1.989 | 2.010 | 2.000 |
| C | 0.078 | 1.989 | 2.000 | 1.989 |
| D | 0.156 | 2.000 | 1.989 | 1.980 |
| E | 0.313 | 2.010 | 1.980 | |
| F | 0.625 | 2.000 | 2.000 | |
| G | 1.250 | 1.980 | 2.000 | |
| H | 2.500 | 1.980 | 2.010 | |

According to the above results, the average fluoride content of the sample 2 was calculated as 1.996 mg/L with standard deviation of 0.010 mg/L and variation coefficient of 0.518%.

It can be seen from the above examples that the kit of the invention for detecting the content of fluoride ions in a microsample has desirable accuracy and reproducibility.

What is claimed is:

1. A kit for detecting content of fluoride ions in a microsample, comprising:
   at least one 96-well plate; and a detecting liquid;
   wherein the at least one 96-well plate comprises 8 main wells which are wells A, B, C, D, E, F, G and H, respectively; the 8 main wells are filled with fluoride solution with different concentrations of fluoride ions; concentrations of the fluoride ions in the 8 main wells are 0 mg/L in well A, 0.039 mg/L in well B, 0.078 mg/L in well C, 0.156 mg/L in well D, 0.313 mg/L in well E, 0.625 mg/L in well F, 1.25 mg/L in well G and 2.5 mg/L in well H, respectively;
   the detecting liquid is a mixture of 7 parts by volume of reagent A, 2 parts by volume of reagent B, 2 parts by volume of reagent C, 2 parts by volume of reagent D and 2 parts by volume of reagent E;
   wherein the reagent A is an analytical acetone; the reagent B is an analytical acetylacetone; the reagent C is a solution having a pH of 5.0 and containing 0.05 mol/L of alizarin complexone; the reagent D is a solution having a pH of 4.1 and containing sodium acetate; and the reagent E is a solution having a pH of 4.1 and containing 0.05 mol/L of lanthanum nitrate.

2. The kit of claim 1, wherein the reagent C is prepared by a method comprising the following steps:
   adding 1.927 g of the alizarin complexone to a 100 mL beaker; adding 5 mL of deionized water by a micropipette; then dropwise adding 5-15 mL of 1 mol/L sodium hydroxide solution to dissolve the alizarin complexone; after the alizarin complexone is dissolved, adding 0.625 g of sodium acetate to produce a mixture, and adjusting the mixture to pH 5.0 with 1 mol/L hydrochloric acid followed by dilution to 100 mL with deionized water to produce the reagent C containing 0.05 mol/L of the alizarin complexone.

3. The kit of claim 1, wherein the reagent D is prepared by a method comprising the following steps:
   dissolving 3.5 g of sodium acetate in 80 mL of deionized water; adding 7.5 mL of glacial acetic acid followed by dilution to 100 mL with deionized water to produce a mixture; and adjusting the mixture to pH 4.1 with an acetic acid solution or a sodium hydroxide solution using a pH meter to produce the reagent D.

4. The kit of claim 1, wherein the reagent E is prepared by a method comprising the following steps:
   weighing 2.215 g of solid lanthanum nitrate; dropwise adding 3-8 mL of a hydrochloric acid solution to dissolve the solid lanthanum nitrate to produce a mixture;
   and adjusting the mixture to pH 4.1 with 1 mol/L sodium acetate followed by dilution to 100 mL with deionized water to obtain the reagent E containing 0.05 mol/L of the lanthanum nitrate.

* * * * *